United States Patent [19]

Gruenfeld

[11] 4,374,847
[45] Feb. 22, 1983

[54] 1-CARBOXYALKANOYLINDOLINE-2-CARBOXYLIC ACIDS

[75] Inventor: Norbert Gruenfeld, White Plains, N.Y.

[73] Assignee: Ciba-Geigy Corporation, Ardsley, N.Y.

[21] Appl. No.: 235,294

[22] Filed: Feb. 17, 1981

Related U.S. Application Data

[63] Continuation-in-part of Ser. No. 200,706, Oct. 27, 1980, abandoned.

[51] Int. Cl.³ .................. A61K 31/405; C07D 209/26
[52] U.S. Cl. .................................. 424/274; 548/430; 548/491
[58] Field of Search ............... 260/326.11 R; 424/274

[56] References Cited

U.S. PATENT DOCUMENTS

| | | | |
|---|---|---|---|
| 3,780,062 | 12/1973 | Kaiser et al. | 260/326.11 R |
| 3,796,723 | 3/1974 | Kaiser et al. | 260/326.11 R |
| 3,974,145 | 8/1976 | Kimura et al. | 424/274 |
| 4,046,889 | 7/1977 | Ondetti et al. | 260/326.2 |
| 4,052,511 | 10/1977 | Cushman et al. | 260/326.2 |
| 4,154,937 | 4/1979 | Cushman et al. | 260/326.2 |
| 4,303,583 | 12/1981 | Kim et al. | 424/274 |
| 4,311,705 | 1/1982 | Ondetti et al. | 424/274 |

FOREIGN PATENT DOCUMENTS

| | | | |
|---|---|---|---|
| 24852 | 3/1981 | European Pat. Off. | 260/326.11 R |
| 37231 | 7/1981 | European Pat. Off. | |
| 31741 | 8/1981 | European Pat. Off. | |
| 55-45664 | 11/1980 | Japan | 260/326.11 R |

OTHER PUBLICATIONS

Y. Omoto et al., Chem. Abst. 65, 15304e, 1966.
Wölcke et al., Helv. Chim. Acta. 53, 1704, (1970).
Patchett et al., Nature, 288, 280, (1980).
Cushman et al., Bioch. 16, 5484, (1977).
Cushman et al., Progress in Cardiovascular Disease 21, 176, (1978).
Amer. Home Prod. Corp. Abstract.

*Primary Examiner*—Jane T. Fan
*Attorney, Agent, or Firm*—Norbert Gruenfeld

[57] ABSTRACT

1-Carboxy-(alkanoyl or aralkanoyl)-indoline-2-carboxylic acids, e.g., those of the formula

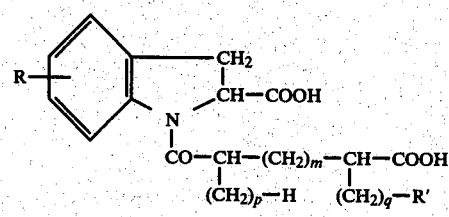

R=H, alkyl, alkoxy, halogeno or $CF_3$;
R′=H or R-phenyl;
m=0 or 1;
p,q=0 to 2;

and functional derivatives thereof, are antihypertensive and cardioactive agents.

17 Claims, No Drawings

1-CARBOXYALKANOYLINDOLINE-2-CARBOXYLIC ACIDS

This is a continuation-in-part of application Ser. No. 200,706, filed Oct. 27, 1980, now abandoned.

BACKGROUND OF THE INVENTION

1-Alkanoylindoline-2-carboxylic acids and their 5,6-dihydroxy-derivatives, i.e., N-acylated Cyclodopa-derivatives, are described in Nippon Kagaku Zasshi 87, 760 (1966) and U.S. Pat. No. 3,796,723 or Helv. Chim. Acta 53, 1701 (1970) respectively, e.g., as synthetical examples of O- and/or N-acylations. Also, 1-carboxyacyl-(azetidine, pyrrolidine or piperidine)-2-carboxylic acids and their functional derivatives are known, e.g., according to U.S. Pat. No. 4,052,511, as possessing antihypertensive activity. Surprisingly it was found that either by introduction of a carboxy group into the former indolines, or by extension of the latter pyrrolidines to the indoline ring-system, superior antihypertensive agents are obtained.

SUMMARY OF THE DISCLOSURE

The present invention concerns and has for its object the provision of new 1-carboxy-(alkanoyl or aralkanoyl)-indoline-2-carboxylic acids, more particularly of those corresponding to Formula I:

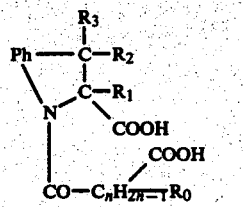

wherein Ph is unsubstituted 1,2-phenylene, or 1,2-phenylene substituted by one to three identical or different members selected from lower alkyl, lower alkoxy, lower alkylenedioxy, hydroxy, halogeno and trifluoromethyl; $R_0$ is hydrogen or HPh; each of $R_1$, $R_2$ and $R_3$ is hydrogen or lower alkyl; and n is an integer from 1 to 10; the amides, mono- or di-lower alkylamides, lower alkyl esters, (amino, mono- or di-lower alkylamino, carboxy or lower carbalkoxy)-lower alkyl esters, or pharmaceutically acceptable salts thereof; as well as of corresponding pharmaceutical compositions and of methods for the preparation and application of said products, which are useful anti-hypertensive and cardioactive agents.

DESCRIPTION OF THE PREFERRED EMBODIMENTS

The 1,2-phenylene group Ph and/or the phenyl group HPh, are preferably unsubstituted or monosubstituted, and their substituents are illustrated by the following groups; lower alkyl, e.g., methyl, ethyl, n- or i-propyl or -butyl; lower alkoxy, e.g., methoxy, ethoxy, n- or i-propoxy or -butoxy; lower alkylenedioxy, e.g., methylenedioxy, 1,1- or 1,2-ethylenedioxy; hydroxy; halogeno, e.g., fluoro, chloro or bromo; or trifluoromethyl.

Each of $R_1$, $R_2$ and $R_3$ is preferably hydrogen, but also lower alkyl, advantageously methyl, or another of those mentioned previously.

The term "lower", referred to above and hereinafter in connection with organic radicals or compounds respectively, defines such with up to 7, preferably up to 4, and advantageously but one or two carbon atoms.

The alkylene or aralkylene moiety $C_n H_{2n-1} R_0$ is either straight, or preferably branched, and contains advantageously up to 8 chain-carbon atoms. Thus, it represents for example, in case $R_0=H$, ethylene, 1,2- or 1,3-propylene, 2-methyl-1,2- or -1,3-propylene, 1,2-, 1,3-, 2,3- or 1,4-butylene, 1,2-, 1,3-, 1,4-, 2,4- or 1,5-pentylene; or in case $R_0=$phenyl, ω-phenyl-(1,2-, 1,3- or 2,3-propylene, -butylene or -pentylene, 1,3-, 2,3- or 2,4-butylene, -pentylene or -hexylene, or 3,5-heptylene or -octylene).

Said functional derivatives, wherein either one or both carboxy groups are esterified or amidized, are preferably the mono- or bis- lower alkyl esters, e.g the methyl, ethyl, n- or i-propyl or -butyl esters; the mono- or bis-amide, or the correspondingly N-alkylated amides, e.g. mono- or dimethylamide, or said substituted lower alkyl esters, preferably the half-esters with a free indoline-2-carboxy group, e.g. the ω-(amino, mono- or dimethylamino, carboxy or carbethoxy)-(ethyl, propyl or butyl) esters.

Pharmaceutically acceptable salts are preferably metal or ammonium salts of said acids, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium bases, e.g., methylamine, diethylamine, triethylamine, dicyclohexylamine, triethanolamine, ethylenediamine, tris-(hydroxymethyl)-aminomethane or benzyl-trimethylammonium hydroxide. Said basic (amino, mono- or di-lower alkylamino)-lower alkyl esters form also acid addition salts, which are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid.

The compounds of this invention exhibit valuable pharmacological properties, primarily hypotensive, antihypertensive and cardioactive effects, inter alia due to their angiotensin converting enzyme inhibitory activity. This is demonstrable by in vivo or in vitro animal tests, using advantageously mammals, e.g., rats, cats, dogs or isolated organs thereof, as test objects. The animals may either be normotensive or hypertensive e.g., genetically hypertensive rats, or renal hypertensive rats and dogs, and sodium-depleted dogs. Said compounds can be applied to them enterally or parenterally, advantageously orally or intravenously, for example within gelatin capsules or in the form of starchy suspensions or aqueous solutions respectively. The applied dosage may range between about 0.01 and 50 mg/kg/day, preferably between about 0.1 and 25 mg/kg/day, advantageously between about 1 and 10 mg/kg/day.

The in vivo lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, the representative members of the compounds of this invention, illustrated by the Examples herein, are very effective in hypertensive rats and dogs at p.o.-doses as low or lower than 10 mg/kg/day.

They also exhibit an inhibitory effect against the angiotensin I pressure response of normotensive rats. The enzyme renin normally causes specific hydrolysis of the circulating protein renin-substrate. This hydrolysis generates angiotensin I, which is further hydrolyzed by the action of said converting enzyme to the potent vasoconstrictor angiotensin II. The inhibition of said enzyme prevents the generation of angiotensin II from I and, therefore, attenuates any pressure response following an angiotensin I challenge.

The corresponding in vivo test is performed with male, normotensive rats, which are anesthetized with 100–120 mg/kg i.p. of sodium ethyl-(1-methylpropyl)-malonylthiourea. A femoral artery and saphenous vein are cannulated for direct blood pressure measurement and i.v. administration of angiotensin I and compounds of this invention. After the basal blood pressure is stabilized, pressor responses to 3 challenges of 0.33 μg/kg of angiotensin I i.v., in 5 minute intervals, are obtained. Such pressure responses are again obtained 5, 10, 15, 30 and 60 minutes after either i.v., or p.o. administration (stomach tube) of the compounds to be tested, and compared with the initial responses. Any observed decrease of said pressor response is an indication of angiotensin I converting enzyme inhibition, ranging up to 80% after 10 mg/kg i.v., or 50 mg/kg p.o. doses, which decrease may be sustained up to 60 minutes.

The in vitro inhibition of the angiotensin-converting enzyme by the compounds of this invention can be demonstrated analogous to Biochim. Biophys. Acta 293, 451 (1973). According to this method said compounds are dissolved at about 1 mM concentrations in phosphate buffer, externally cooled with ice. To these solutions various μl amounts of 1 mM of histidyl-leucine in phosphate buffer are added, followed by 100 μl of 5 mM hippuryl-histidyl-leucine in phosphate buffer and 50 μl of the angiotensin-converting enzyme, which is freshly prepared from lungs of adult male rabbits in Tris buffer, containing potassium and magnesium chloride, as well as sucrose. Said solutions are incubated at 37° for 30 minutes and combined with 0.75 ml of 0.6 N aqueous sodium hydroxide to stop further reaction. Then 100 μl of o-phthalaldehyde are added at room temperature, and 10 minutes later 100 μl of 6 N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the $IC_{50}$, i.e., the drug concentration which gives half the activity of the control sample containing no drug. Again, said representative members of the compounds of this invention are very effective in this in vitro test system, down to $IC_{50}$ values as low or lower than 39 nM.

Accordingly, the compounds of this invention are valuable antihypertensive agents, especially useful for ameliorating hypertension (regardless of etiology) and/or heart-conditions, such as congestive heart failure, and/or other edemic or ascitic diseases, e.g. hepatic cirrhosis. They are also useful intermediates in the preparation of other valuable products, especially of corresponding pharmaceutical compositions.

Particularly useful for said purpose are those compounds of Formula I, wherein Ph is unsubstituted 1,2-phenylene, or 1,2-phenylene substituted by one or two identical or different members selected from lower alkyl, lower alkoxy, hydroxy and halogeno, or 1,2-phenylene substituted by one lower alkylenedioxy or trifluoromethyl group; $R_o$ is hydrogen or HPh; each of $R_1$, $R_2$ and $R_3$ is hydrogen or lower alkyl; and n is an integer from 1 to 10; the amides, mono- or di-lower alkylamides, lower alkyl esters, (amino, mono- or di-lower alkylamino, carboxy or lower carbalkoxy)-lower alkyl esters, or pharmaceutically acceptable alkali metal, alkaline earth metal or ammonium salts of said acids, or acid addition salts of said aminoalkyl esters.

More preferred are those compounds of Formula I, wherein Ph is 1,2-phenylene, unsubstituted or monosubstituted by lower alkyl, lower alkoxy, lower alkylenedioxy, hydroxy, halogeno or trifluoromethyl; $R_o$ is hydrogen or HPh; each of $R_1$, $R_2$ and $R_3$ is hydrogen or methyl; and n is an integer from 2 to 8; and said functional acid and amino derivatives listed in the previous paragraph.

Especially valuable compounds of this invention are those of Formula II

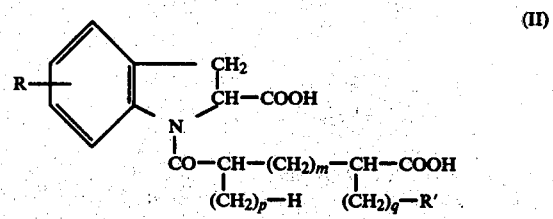

more specifically the indoline-2S-chiral epimers thereof, wherein R is hydrogen, alkyl or alkoxy with up to 4 carbon atoms, halogeno or trifluoromethyl; m is the integer 0 or 1; each of p and q is an integer from 0 to 2; and R' is hydrogen or R-phenyl; the mono- or bis-amide, the mono- or bis-lower (alkyl or ω-aminoalkyl) esters, pharmaceutically acceptable alkali metal or ammonium salts of said acids or acid addition salts of said aminoalkyl esters.

The most preferred compounds of this invention are those of Formula II, wherein R is hydrogen, methyl, methoxy, fluoro, chloro or trifluoromethyl, advantageously in the 5-position, each of m and p is the integer 1, q is the integer 1 or 2, and R' is hydrogen or phenyl, or said functional acid and amino derivatives listed in the preceding paragraph.

The compounds of this invention are prepared according to conventional methods, advantageously by:

(1) condensing a compound of Formula III

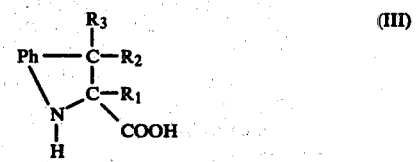

or said acid or amino derivatives thereof, with a reactive functional derivative of a compound of Formula IV

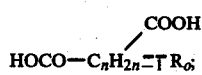

(2) hydrolysing or alcoholyzing a compound of Formula V

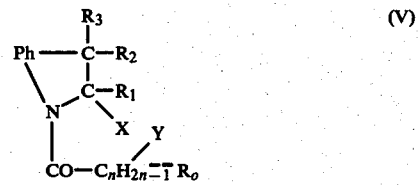

wherein at least one of X and Y is cyano, and the other is said free, amidized or esterified carboxy group; or (3) hydrogenating in a compound of Formula VI

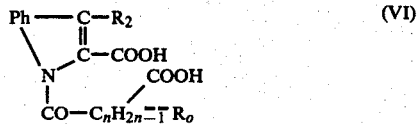

or said acid or amino derivatives thereof, the indole moiety of the indoline moiety; and, if desired, converting any resulting compound into another compound of this invention.

Reactive functional derivatives of compounds IV are preferably ester-halides, simple or mixed anhydrides, such as the lower alkyl half esters of said acid chlorides, the cyclic anhydride, or mixed acetic or cyanoacetic anhydrides. Said condensation of compounds III and IV occurs either spontaneously, or in the presence of condensing agents, such as organic or inorganic bases, e.g. said salt-forming amines or alkali metal carbonates, or disubstituted carbodiimides.

Said hydrolysis of the nitriles V to the corresponding acids or amides is advantageously carried out with inorganic acids, such as hydrohalic or sulfuric acids, in known manner; and said alcoholysis is analogously performed in the presence of both said acids and the corresponding unsubstituted or substituted lower alkanols.

Finally, said hydrogenation of the indoles VI to the indolines I is also performed according to conventional hydrogenations of 1-acyl-indoles, for example, with catalytically activated or nascent hydrogen, e.g. hydrogen in the presence of platinum, palladium, rhodium or nickel catalysts, or hydrogen generated electrolytically, or by the action of metals on acids or alcohols. Also reducing agents may be used, such as simple or complex light metal hydrides, e.g. boranes, or advantageously alkali metal borohydrides or cyanoborohydrides. Preferred is the asymmetric hydrogenation to the indoline-2S-carboxylic acids, or said derivatives thereof, with chiral catalysts, as, for example, prepared from a rhodium salt with (R)-1,2-bis-(diphenylphosphino)-propane on (R)-1,2-bis(o-anisylphenylphosphino)-ethane and 1,5-cyclooctadiene.

The compounds of the invention so obtained, can be converted into each other according to conventional methods. Thus, for example, resulting amides or esters may be further hydrolyzed or alcoholyzed (transesterified) according to process (2), or with aqueous alkalies, such as alkali metal carbonates or hydroxides, respectively. Resulting free acids may be esterified with said unsubstituted or substituted lower alkanols or diazoalkanes, or converted into said metal, ammonium or acid addition salts in conventional manner.

Thus, for example, any resulting free acid or base can be converted into a corresponding metal, ammonium or acid addition salt respectively, by reacting it with an equivalent amount of the corresponding base, basic salt, acid or ion exchange preparation, e.g. said acids with alkali or ammonium hydroxides or carbonates, or said aminoalkyl esters with said inorganic or organic acids respectively. Any resulting salt may also be converted into the free compounds, by liberating the latter with stronger acids or bases respectively. In view of the close relationship between the free compounds, and the salts thereof, whenever a compound of the invention, or intermediate thereof, is referred to in this context, a corresponding salt is also intended, provided such is possible or appropriate under the circumstances.

The starting material of Formulae III and IV is known, or, if new, may be prepared according to conventional methods, e.g., those illustrated by the examples herein. Compounds of Formula V, are also obtained according to conventional methods, e.g., by condensing the corresponding nitriles of Formulae III and/or IV according to said process 1.

In case mixtures of geometrical or optical isomers of the above compounds of Formulae I to V are obtained, these can be separated into the single isomers by methods in themselves known, e.g., by fractional distillation, crystallization and/or chromatography. Racemic products can likewise be resolved into the optical antipodes, for example, by separation of diastereomeric salts thereof, such as according to J. Org. Chem. 43, 3803 (1978), e.g., by the fractional crystallization of d- or l-(tartrates, mandelates, camphorsulfonates, or 1-naphthyl-1-ethylisocyanates), or of d- or l-(α-methylbenzylammonium, cinchonidine, cinchonine, quinine, quinidine, ephedrine, dehydroabiethylamine, brucine or strychnine)-salts. The preferred starting material of Formula III is the 2-S-optical isomer (epimer) thereof.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably at the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g., those of Formula II, and being the following chiral isomers:

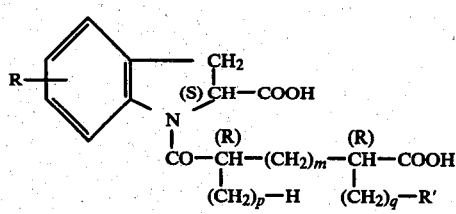

(IIa)

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, or effervescent mixtures and/or (e) absorbents, colorants, flavors and sweeteners. Injectable compositions are preferably aqueous isotonic solutions or suspensions; and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances, e.g. other anti-hypertensive agents and/or diuretics. Said compositions are prepared according to conventional mixing, granulating or coating methods respectively, and contain about 0.1 to 75%, preferably about 1 to 50% of the active ingredient. A unit dosage for a mammal of about 50–70 kg weight may contain between about 5 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To the suspension of 5.0 g of indoline-2S-carboxylic acid ethyl ester hydrochloride, 9.1 g of powdered potassium carbonate and 45 ml of methylene chloride, 3.61 g of methyl glutaroyl chloride in 5 ml of methylene chloride are added while stirring at room temperature. The mixture is stirred overnight at room temperature, cooled with ice, and 100 ml of water are added. The organic layer is separated, washed with N-hydrochloric acid and water, dried and evaporated, to yield the 1-(4-carbomethoxybutanoyl)-indoline-2S-carboxylic acid ethyl ester melting at 88°–90°.

The starting material is prepared as follows: 120 g of 1-acetylindoline-2-carboxylic acid [Nippon Kagaku Zasshi 87, 760 (1966)] and 172 g of l-cinchonidine are dissolved in 1,200 ml of hot ethanol. The solution is allowed to stand at room temperature overnight and then at 0° for 4 days. The white crystalline salt is filtered off and discarded. The filtrate is evaporated, 1,000 ml of water are added and the solution is adjusted to pH=1 with concentrated hydrochloric acid. After 15 minutes the product is collected by filtration and washed thrice with 250 ml of 2 N aqueous hydrochloric acid, twice with 500 ml of water and twice with 100 ml of ethanol, to give the 1-acetylindoline-2S-carboxylic acid melting at 214°–215°; $[\alpha]_D = -133.3°$ (c=1.165 in ethanol).

The suspension of 37.5 g thereof in 380 ml of 2 N aqueous hydrochloric acid is deoxygenated by bubbling nitrogen through it for 5 minutes, followed by refluxing for 2 hours. It is cooled to room temperature, filtered through infusorial earth, the filtrate evaporated and the residue crystallized from diethyl ether-isopropanol, to yield the indoline-2S-carboxylic acid hydrochloride melting at 133° (dec.); $[\alpha]_D = -70.4°$ (c=1 in ethanol).

The solution of 34 g thereof in 350 ml of ethanol is saturated with dry hydrogen chloride without external cooling. The mixture is stirred for 2 hours at room temperature and the solvent removed until crystallization begins. The concentrate is poured into 400 ml of diethyl ether, cooled at 0° for 1 hour and filtered, to yield the indoline-2S-carboxylic acid ethyl ester hydrochloride melting at 179°–181°; $[\alpha]_D = -63°$ (c=1.385 in ethanol).

EXAMPLE 2

To the suspension of 5.0 g of 1-(4-carbomethoxybutanoyl)-indoline-2S-carboxylic acid ethyl ester in 47 ml of methanol is added 47 ml of N aqueous sodium hydroxide and the mixture is stirred at room temperature for 4 hours. It is concentrated at room temperature and reduced pressure, the aqueous solution acidified with concentrated hydrochloric acid while cooling, the resulting precipitate collected, washed with water and dried, to yield the 1-(4-carboxybutanoyl)-indoline-2S-carboxylic acid melting at 175°–177°; $[\alpha]_D = -97.8°$ (c=1.0 in ethanol).

EXAMPLE 3

To the solution of 11 g of indoline-2S-carboxylic acid hydrochloride in 75 ml of pyridine, 8.25 g of 4-carbomethoxy-2-methylbutanoyl chloride are added and the mixture is stirred at room temperature overnight. The pyridine is distilled off at room temperature and reduced pressure, the residue is cooled, acidified with 3 N hydrochloric acid and extracted with methylene chloride. The extract is evaporated, the residue dissolved in diethyl ether and the solution combined with that of 10 ml of dicyclohexylamine in 125 ml of hexane. The precipitate is collected, washed with hot ethyl acetate and suspended in acetone overnight, to yield the dicyclohexylammonium 1-(4-carbomethoxy-2-methylbutanoyl)-indoline-2S-carboxylate, melting at 203°–205°; the corresponding free acid melts at 97°–99°.

The first starting material is described as intermediate in Example 1, and the second may be prepared as follows:

9.64 g of oxalyl chloride are added to the solution of 6.1 g of 4-carbomethoxy-2-methylbutanoic acid (U.S. Pat. No. 4,052,511) in 50 ml of methylene chloride. The mixture is refluxed for two hours and evaporated, to yield the 4-carbomethoxy-2-methylbutanoyl chloride, which is used as such without further purification.

EXAMPLE 4

The solution of 2.03 g of indoline-2S-carboxylic acid ethyl ester and 2.5 g of 2-(2-phenethyl)-glutaric acid anhydride in 75 ml of toluene, is heated to 70° overnight under nitrogen. It is evaporated, the residue dissolved in diethyl ether, the solution washed with N hydrochloric acid and extracted with saturated aqueous sodium bicarbonate. The extract is cooled, acidified with hydrochloric acid and re-extracted with methylene chloride. The organic extract is evaporated, the residue dissolved in diethyl ether and the solution combined with that of 1.2 ml of dicyclohexylamine in 25 ml of hexane. The resulting precipitate is filtered off and washed with hexane, to yield the dicyclohexylammonium 1-[4-carboxy-4-(2-phenethyl)-butanoyl]-indoline-2S-carboxylic acid ethyl ester, melting at 132°–134°. It may be re-converted to the free acid with N hydrochloric acid.

The starting material is prepared as follows: 29.8 g of indoline-2S-carboxylic acid ethyl ester hydrochloride are partitioned between 300 ml of saturated aqueous sodium bicarbonate and 100 ml of methylene chloride. The aqueous layer is extracted twice with additional 200 ml of methylene chloride, the combined organic layers washed with saturated aqueous sodium chloride and evaporated, to yield the indoline-2S-carboxylic acid ethyl ester as an oil, showing the major IR-band at 1730 $cm^{-1}$.

The solution of 12 g of 2-(2-phenyethyl)-glutaric acid [J Chem. Soc. 1950, 1683] in 75 ml of acetic acid anhydride is refluxed for 4 hours and evaporated. The residue is crystallized from diethyl ether, to yield the corresponding anhydride melting at 78°–80°.

EXAMPLE 5

The solution of 2.4 g of 1-[4-carboxy-4-(2-phenethyl)-butanoyl]-indoline-2S-carboxylic acid ethyl ester in 17.6 ml of methanol and 17.6 ml of N aqueous sodium hydroxide is stirred at room temperature for 2.5 hours. It is concentrated at room temperature under reduced pressure, the aqueous solution filtered, acidified with hydrochloric acid and extracted with methylene chloride. The extract is evaporated and the residue crystallized from petroleum ether, to yield the 1-[4-carboxy-B 4-(2-phenethyl)-butanoyl]-indoline-2S-carboxylic acid melting at 136°–138°.

EXAMPLE 6

According to the methods illustrated by the previous examples, the following 1-(carboxyalkanoyl or -aralkanoyl)-indoline-2S-carboxylic acids of Formula I, with Ph=1,2-phenylene and $R_1=R_2=R_3=H$, as well as said derivatives thereof, are prepared:

| No | $C_nH_{2n-1}R_o$ | $C_nH_{2n-1}R_o-$ COOH deriv. | Indoline-2-COOH der. | m.p. °C. or NMR |
|---|---|---|---|---|
| 1 | CH—CH$_2$<br>\|<br>CH$_3$ | — | — | 122–124°, 83–85° for hemihydrate |
| 2 | (CH$_2$)$_2$—CH<br>\|<br>CH$_3$ | — | ethyl ester | 104–106° |
| 3 | " | — | — | 172–174° |
| 4 | CH—(CH$_2$)$_2$<br>\|<br>CH$_3$ | methyl ester | ethyl ester | 4.25, 3.65 1.30 ppm |
| 5 | " | — | — | 72–74° |
| 6 | CH$_2$—CH—CH$_2$<br>\|<br>CH$_3$ | — | ethyl ester | 111–113° |
| 7 | " | — | — | 125–127° |
| 8 | CH—CH$_2$—CH<br>\|  \|<br>CH$_3$  CH$_3$<br>(erythro) | — | ethyl ester-D | 132–134° |
| 9 | " | — | — | 58–60° |
| 10 | CH—CH$_2$—CH<br>\|  \|<br>CH$_3$  CH$_3$<br>(threo) | — | — | 70–72° |
| 11 | CH—CH$_2$—CH<br>\|  \|<br>CH$_3$  (CH$_2$)$_2$)—C$_6$H$_5$<br>(erythro) | — | — | 1.17, 1.32 ppm |

-continued

| No | $C_nH_{2n-1}R_o$ | $C_nH_{2n-1}R_o-$COOH deriv. | Indoline-2-COOH der. | m.p. °C. or NMR |
|---|---|---|---|---|
| 12 | CH—CH₂—CH<br>\|           \|<br>CH₃  (CH₂)₂)—C₆H₅<br>(threo) | — | — | 1.15, 1.25 ppm |

D = dicyclohexylammonium salt

The starting materials for said compounds 1, 2, 4, 6, 11 and 12 are the 3-carbomethoxy-2-methylpropanoyl chloride, 2-methylglutaric anhydride, 4-carbomethoxy-2-methylbutanoyl chloride, 3-methylglutaric anhydride and the erythro or threo 4-carbomethoxy-4-(2-phenethyl)-2-methylbutanoyl chloride respectively. That of compounds 8 and 9 may be prepared as follows: The solution of 6.0 g of meso-2,4-dimethylglutaric acid anhydride [J. Am. Chem. Soc. 77, 1862 (1955)] in 4 ml of methanol is refluxed for one hour and evaporated, to yield the erythro-4-carbomethoxy-2,4-dimethylbutanoic acid. It is converted into the acid chloride by refluxing it with 10.9 g of oxalyl chloride in 50 ml of methylene chloride for 2 hours, and evaporating said mixture.

The corresponding threo-isomer is analogously obtained from the racemic anhydride.

EXAMPLE 7

The solution of 1 g of 1-(4-carbomethoxy-2-methylbutanoyl)-indoline-2S-carboxylic acid (Example 3) in 10 ml of methanol is saturated with ammonia at 0° and stored in a pressure bottle at room temperature for 4 days. It is evaporated, the residue taken up in water, the mixture acidified with 2 N hydrochloric acid at 0° and the addition of a few drops of methylene chloride initiates crystallization. The mixture is filtered and the residue triturated with diethyl ether, to yield the 1-(4-carbamoyl-2-methylbutanoyl)-indoline-2S-carboxylic acid melting at 192°–194°.

EXAMPLE 8

(a) To a solution of 1.43 g of indoline-2S-carboxylic acid hydrochloride in 15 ml pyridine at 0° C. is added 1.35 g of 4-carboethoxy-2R,4R-dimethylbutanoyl chloride. The reaction mixture is stirred at room temperature for 3 hours and evaporated under vacuum. The residue is treated with 20 ml of 3 N hydrochloric acid and extracted three times with 10 ml of methylene chloride and the extract is evaporated to dryness. The 1-(4-carboethoxy-2R,4R-dimethylbutanoyl)indoline-2S-carboxylic acid obtained is dissolved in 75 ml of ether and treated with 2.2 ml dicyclohexylamine to yield the crystalline dicyclohexylammonium salt. This is slurried in a mixture of 40 ml of ethyl acetate and 45 ml of 5% aqueous potassium bisulfate solution for 1 hour. The ethyl acetate layer is separated, washed with water, dried over sodium sulfate, and evaporated to dryness. Crystallization form hexane yields 1-(4-carboethoxy-2R,4R-dimethylbutanoyl)indoline-2S-carboxylic acid, melting at 125°–7°, $[\alpha]_D = -159°$ (C=0.2 in ethanol).

(b) By using 4-carboethoxy-2R-methylbutanoyl chloride instead of the 4-carboethoxy-2R,4R-dimethylbutanoyl chloride as described above, one obtains 1-(4-carboethoxy-2R-methylbutanoyl)-indoline-2S-carboxylic acid, melting at 133°–135° C., $[\alpha]_D = -120.5°$ (C=0.2 in ethanol).

(c) Similarly prepared is 1-(4-carboethoxy-2R-isopropylbutanoyl)indoline-2S-carboxylic acid.

(d) Prepared similarly are 1-(4-carboethoxy-2R,4R-dimethyl-butanoyl)indoline-2S-carboxylic acids wherein the 5-position of the indoline nucleus is substituted by either methoxy, chloro or methyl.

The starting materials are prepared as follows:

A solution of 3.7 g of 2R-methylglutaric acid [J. Am. Chem. Soc. 77, 3383 (1955)] in 10 ml of acetyl chloride is stirred at 50° for 2 hours. The reaction mixture is evaporated to dryness to yield the 2R-methylglutaric anhydride, melting at 50°–2°, $[\alpha]_D = +43.8°$ (C=1.0 in chloroform). 2R,4R-dimethylglutaric anhydride, melting at 43°–5°, $[\alpha]_D = +56.5°$ (C=1.0, chloroform) is prepared in identical fashion from 2R, 4R-dimethylglutaric acid [Arkiv Kemi Mineral Geol. B14, 1 (1940), $[\alpha]_D = -35.5°$ (C=2.0 in ethanol].

Similarly prepared is the 2R-isopropylglutaric anhydride from the corresponding 2R-isopropylglutaric acid [Arkiv Kemi Mineral. Geol. B23, 1 (1946)].

A solution of 1.7 g of 2R,4R-dimethylglutaric anhydride in 40 ml of absolute ethanol is heated under reflux overnight and evaporated to dryness to yield 4-carboethoxy-2R,4R-dimethylbutanoic acid as an oil, $[\alpha]_D = -49.4°$ (c=1.0 in ethanol).

A solution of 2.9 g of 2R-methylglutaric anhydride in 10 ml of ethanol is refluxed for 3 hours and evaporated to dryness. A solution of the oil in 25 ml of ether is treated with 5.0 ml of dicyclohexylamine in 25 ml of hexane to yield the 4-carboethoxy-2R-methylbutanoic acid as the dicyclohexylammonium salt, m.p. 98°–100°. Conversion to the free acid with 1 N hydrochloric acid and extraction with ethyl acetate gives 4-carboethoxy-2R-methylbutanoic acid as an oil, $[\alpha]_D = -20.9°$ (c=1.0 in chloroform).

A solution of 1.27 g of 4-carboethoxy-2R,4R-dimethylbutanoic acid in 15 ml of methylene chloride is treated with 1.7 g of oxalyl chloride, heated under reflux for 3 hours and evaporated to dryness to yield 4-carboethoxy-2R,4R-dimethylbutanoyl chloride, NMR peaks at 1.8, 2.5, 2.8, 4.1 ppm. Similarly prepared are the 4-carboethoxy-2R-methylbutanoyl chloride (NMR peaks at 2.0, 2.4, 4.3 ppm) and the 4-carboethoxy-2R-isopropylbutanoyl chloride.

5-methoxyindoline-2-carboxylic acid, 5-chloro-indoline-2-carboxylic acid, and 5-methylindoline-2-carboxylic acid can be prepared from the corresponding substituted indole-2-carboxylic acid according to the method described for Example 1.

EXAMPLE 9

(a) To a solution of 2.63 g of ethyl indoline-2S-carboxylate in 40 ml of methylene chloride containing 4.8 g of anhydrous potassium carbonate is added 2.39 g of 4-carboethoxy-2R,4R-dimethylbutanoyl chloride. The reaction is stirred overnight at room temperature and then extracted with 20 ml of water. The organic layer is washed with 15 ml of 1 N hydrochloric acid and 15 ml of water, dried (Na$_2$SO$_4$) and evaporated to give ethyl 1-(4-carboethoxy-2R,4R-dimethylbutanoyl)-indoline-2S-carboxylate as an oil having $[\alpha]_D = -130.10$ (c=1.0 in ethanol).

(b) Similarly prepared is ethyl 1-(4-carboethoxy-2R-methylbutanoyl)-indoline-2S-carboxylate as an oil having NMR peaks at 1.2, 4.1 to 4.3, 4.9, 6.7 and 7.2 ppm, using 4-carboethoxy-2R-methylbutanoyl chloride as the acylating reagent.

EXAMPLE 10

To a solution of 3.2 g of ethyl indoline-2S-carboxylate hydrochloride and 1.47 g of triethylamine in 60 ml of methylene chloride is added 2.34 g of 4-carboethoxy-2R-methylbutanoic acid followed by 2.97 g of 1-(3-dimethylaminopropyl)-3-ethylcarbodiimide hydrochloride. The reaction is stirred at room temperature for 3 days and poured into water. The organic layer is separated and washed successively with 30 ml of B 1 N hydrochloric acid, 30 ml of water and 30 ml of 10% aqueous sodium bicarbonate solution. The organic layer is dried over sodium sulfate and evaporated to dryness to yield ethyl 1-(4-carboethoxy-2R-methylbutanoyl)-indoline-2S-carboxylate identical to the compound of example 9(b).

EXAMPLE 11

A solution of 0.45 g of ethyl indoline-2S-carboxylate and 0.30 g of 2R,4R-dimethylglutaric anhydride in 10 ml of toluene is stirred at 70° for 18 hours. The reaction is cooled to room temperature, washed twice with 5 ml of 1 N hydrochloric acid and extracted twice with 10 ml of 5% sodium bicarbonate. The combined bicarbonate portions are acidified with 4.0 ml of 12 N hydrochloric acid and extracted three times with 10 ml of methylene chloride. The combined methylene chloride portions are dried over Na$_2$SO$_4$ and evaporated to give ethyl 1-(4-carboxy-2R,4R-dimethyl-butanoyl)-indoline-2S-carboxylate as an oil having NMR peaks at 1.0 to 1.3, 4.15, 5.10, 7.2 and 8.4 ppm.

EXAMPLE 12

(a) To a solution of 3.4 g of ethyl 1-(4-carboethoxy-2R,4R-dimethyl-butanoyl)-indoline-2S-carboxylate in 30 ml of methanol is added 28.2 ml of 1 N aqueous sodium hydroxide solution. The reaction mixture is stirred at room temperature for 4 hours, evaporated to remove methanol and acidified with 3.5 ml of cencentrated hydrochloric acid. The mixture is extracted four times with 10 ml of methylene chloride. The combined extract is dried over sodium sulfate and evaporated to dryness and the residue is recrystallized from ether-petroleum ether to give 1-(4-carboxy-2R,4R-dimethyl-butanoyl)-indoline-2S-carboxylic acid melting at 132°-134°, $[\alpha]_D = -144°$ (c=1.0 in ethanol).

Similar hydrolysis of 0.46 g of ethyl 1-(4-carboxy-2R,4R-dimethylbutanoyl)-indoline-2S-carboxylate (example 10) and crystallization of the product from water yields the 1-(4-carboxy-2R,4R-dimethylbutanoyl)indoline-2S-carboxylic acid hydrate having a melting point of 93°-95°, $[\alpha]_D = -142.8°$ (c=1.0 in ethanol).

(b) Similarly, hydrolysis of ethyl 1-(4-carboethoxy-2R-methylbutanoyl)indoline-2S-carboxylate yields 1-(4-carboxy-2R-methylbutanoyl)-indoline-2S-carboxylic acid, crystallized from ether and melting at 147°-9°, $[\alpha]_D = -125°$ (c=0.2 in ethanol). Similarly, hydrolysis of 1-(4-carboethoxy-2R-methylbutanoyl)-indoline-2S-carboxylic acid yields the diacid identical to the 1-(4-carboxy-2R-methylbutanoyl)-indoline-2S-carboxylic acid isolated above.

EXAMPLE 13

A solution of 90 mg of indoline-2-S-carboxylic acid hydrochloride is treated with 92 mg of 4-carboethoxy-2R-methyl-4R-phenethylbutanoyl chloride in pyridine by the analogous process described in detail for Example 8 to yield 1-(4-carboethoxy-2R-methyl-4R-phenethylbutanoyl)indoline-2S-carboxylic acid as the dicyclohexylamine salt melting at 146°-149°.

The starting material is prepared in part according to the general process described in Tetrahedron Letters 1980, 4233-6, as follows:

Aqueous sodium hydroxide (1 N, 25 ml) is added to a solution of 2.0 g of L-prolinol (U.S. patent 3,935,280) in 50 ml of CH$_2$Cl$_2$. After cooling the reaction mixture to 0° C., 4.0 g of 4-phenylbutyric acid chloride is added and the reaction is stirred vigorously for 4 hours at 0° C., followed by 1 hour at room temperature. The reaction is diluted with an equal volume of CH$_2$Cl$_2$ and the layers separated. The organic phase is washed with 30 ml of water and dried over Na$_2$SO$_4$/K$_2$CO$_3$. The solvent is evaporated to yield 4.4 g of N-(4-phenylbutanoyl)-L-prolinol having IR peaks at 3280 and 1605 cm$^{-1}$, $[\alpha]_D^{25} = -40.3°$ (methanol). 20.5 g of N-methyl-N,N'-dicyclohexylcarbodiimidium iodide (Angew, Chem., Int. Ed. 11, 229 (1972) is added to a solution of 5.3 of R-(−)-3-benzyloxy-2-methylpropanol (Helv. Chim. Acta 60, 925 (1977) in 200 ml dry tetrahydrofuran under nitrogen and the reaction is stirred at room temperature for 14 hours. The solvent is evaporated and 20 ml of ether and 5 ml of pentane are added. The resulting yellow solid is collected and the mother liquors are chromatographed on 200 g of silica gel with pentane to yield 6.68 g of the S(+)-3-benzyloxy-2-methylpropyl iodide having Rf=0.60 (9:1 of pentane:ether/Si°$_2$), $[\alpha]_D^{25} = +11.1°$ (MeOH). N-(4-phenylbutanoyl) L-prolinol is dissolved in 2 ml of dry tetrahydrofuran and added dropwise to a solution of lithium diisopropylamide (15.6 m moles) in 50 ml of tetrahydrofuran at 0° C. under nitrogen. After 30 minutes at 0° C., 2.03 g of S-(+)-3-benzyloxy-2-methylpropyl iodide is added dropwise in 2 ml of dry tetrahydrofuran. The reaction is stirred at 0° C. for 5 hours, at −15° C. for 15 hours and quenched at 0° C. with excess saturated ammonium chloride solution. The reaction mixture is diluted with 30 ml of ether. The layers are separated and the organic phase is washed with 16 ml of 1 N HCl, 15 ml of brine, 15 ml of saturated sodium bicarbonate and dried over sodium sulfate. Evaporation of solvent yields 3.6 g of an oil which is filtered through 60 g of silica gel with ethyl acetate to yield 2.3 g of N-(R,R-5-benzyloxy-4-methyl-2-phenethylpentanoyl) L-prolinol having Rf 0.51 (EtoAc/SiO$_2$).

A solution of 2.0 g of N-(R,R-5-benzyloxy-4-methyl-2-phenethyl pentanoyl) L-prolinol in 50 ml of 1 N ethanolic hydrochloric acid is refluxed under nitrogen for 15 hours. The solvent is evaporated and the residue is chromatographed on 60 g of silica gel with pentane:ether (2:1) to yield 0.65 g of ethyl R,R-5-benzyloxy-4-methyl-2-phenethylpentaoate having Rf 0.37 (9:1 of pentane:ether/SiO$_2$), $[\alpha]_D^{25} + 2.85$ (E+OH).

A solution of 0.6 g of ethyl R,R-5-benzyloxy-4-methyl-2-phenethylpentanoate in 50 ml of anhydrous ethanol is hydrogenated at 40 psi for 3 hours at room temperature with 0.5 g of 5% palladium on charcoal catalyst. The catalyst is then removed by filtering through celite and the solvent is evaporated to yield 0.41 g of ethyl R,R-5-hydroxy-4-methyl-2-phenethylpentanoate having Rf=0.36 (1:1 of pentane-ether).

Ethyl R,R-5-hydroxy-4-methyl-2-phenethylpentanoate (0.35 g) is dissolved in 15 ml of dry dimethylformamide at room temperature under nitrogen. Pyridinium dichromate (2.5 g) is added and the reaction mixture is stirred for 15 hours at room temperature before being poured into 150 ml of water. The aqueous solution is extracted with ether (4×40 ml). The ethereal extracts are washed with 30 ml of water and the three times with 20 ml of a 1:1 solution of sodium bicarbonate: potassium carbonate (pH=10.5). The basic wash is acidified to pH=2 with concentrated sulfuric acid, while keeping the temperature between 5° and 10° C., and extracted with ether (4×20 ml). The ethereal extracts are washed with 20 ml of brine and dried over $Na_2SO_4/MgSO_4$. Evaporation of the solvent yields 0.28 g of 4-carboethoxy-2R-methyl-4R-(phenethyl)butanoic acid, having Rf=0.50 (99:1:100 of ether:AcOH:hexane), $[\alpha]_D^{25} -4.91°$ (EtOH)

Treatment of 4-carboethoxy-2R-methyl-4R-(phenethyl)butanoic acid with oxalyl chloride in methylene chloride yields 4-carboethoxy-2R-methyl-4R-phenethyl-butanoyl chloride.

EXAMPLE 14

According to the process described for example 10, 79 mg of ethyl indoline-2S-carboxylate hydrochloride is reacted with 96.5 mg of 4-carboethoxy-2R-methyl-4R-(phenethyl)butanoic acid (See example 13) in the presence of 0.05 ml of triethylamine and 66.5 mg of 1-(3-dimethylaminopropyl)-3-ethylcarbodiimide hydrochloride to yield ethyl 1-(4-carboethoxy-2R-methyl-4R-phenethylbutanoyl) indoline-2S-carboxylate having Rf=0.6 (9:1 $CHCl_3CH_3OH/SiO_2$).

To a solution of 87 mg of the above diester in 4 ml of methanol at room temperature is added 0.2 ml of 2.2 N aqueous potassium hydroxide, 1.5 ml of water and the reaction mixture is stirred at room temperature for 2 hours. The reaction mixture is worked up in the usual manner (see Example 12) to yield 1-(4-carboethoxy-2R-methyl-4R-phenethylbutanoyl)indoline-2S-carboxylic acid purified as the dicyclohexylamine salt melting at 145°–8° and identical to compound of example 13.

Further basic hydrolysis yields 1-(4-carboxy-2R-methyl-4R-phenethylbutanoyl)indoline-2S-carboxylic acid.

EXAMPLE 15

Preparation of 10,000 tablets each containing 5 mg of the active ingredient of Example 5:

| Formula: | |
| --- | --- |
| 1-[4-carboxy-4-(2-phenethyl)-butanoyl]-indoline-2S-carboxylic acid | 50.00 g |
| Lactose | 1,157.00 g |
| Corn starch | 75.00 g |
| Polyethylene glycol 6,000 | 75.00 g |
| Talcum powder | 5.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 16

Preparation of 10,000 capsules each containing 10 mg of the active ingredient of Example 2:

| Formula | |
| --- | --- |
| 1-(4-carboethoxy-2R,4R-dimethylbutanoyl) indoline-2S-carboxylic acid | 100.0 g |
| Lactose | 1,800.0 g |
| Talcum powder | 100.0 g |

Procedure:

All the powders are passed through a screen with openings of 0.6 mm. Then the drug substance is placed in a suitable mixer and mixed first with the talcum, then with the lactose until homogeneous. No. 3 capsules are filled with 200 mg, using a capsule filling machine. Analogously tablets or capsules are prepared from the remaining compounds of the invention, e.g., those illustrated by the other examples herein.

I claim:

1. A 1-carboxy-(alkanoyl or aralkanoyl)-indoline-2-carboxylic acid compound of the formula:

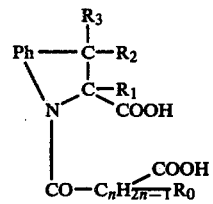

wherein Ph is unsubstituted 1,2-phenylene, or 1,2-phenylene substituted by one to three identical or different members selected from lower alkyl, lower alkoxy, lower alkylenedioxy, hydroxy, halogeno and trifluoromethyl; $R_o$ is hydrogen or HPh; each of $R_1$, $R_2$ and $R_3$ is hydrogen or lower alkyl; and n is an integer from 2 to 8; an amide, mono- or di-lower alkylamide, lower alkyl ester, (amino, mono- or di-lower alkylamino, carboxy or lower carbalkoxy)-lower alkyl ester, or a pharmaceutically acceptable salt thereof.

2. A compound as claimed in claim 1, in which formula Ph is unsubstituted 1,2-phenylene, or 1,2-phenylene substituted by one or two identical or different members selected from lower alkyl, lower alkoxy, hydroxy and halogeno, or 1,2-phenylene substituted by one lower alkylenedioxy or trifluoromethyl group; $R_o$ is hydrogen or HPh; each of $R_1$, $R_2$ and $R_3$ is hydrogen or lower alkyl; and n is an integer from 2 to 8; an amide, mono- or di-lower alkylamide, a lower alkyl ester, (amino, mono- or di-lower alkylamino, carboxy or lower carbalkoxy)-lower alkyl ester; or a pharmaceutically acceptable alkali metal, alkaline earth metal or ammonium salt of said acid, or an acid addition salt of said aminoalkyl ester.

3. A compound as claimed in claim 2, wherein Ph is 1,2-phenylene, unsubstituted or mono-substituted by lower alkyl, lower alkoxy, lower alkylenedioxy, hydroxy, halogeno or trifluoromethyl; $R_o$ is hydrogen or HPh; each $R_1$, $R_2$ and $R_3$ is hydrogen or methyl; and n is an integer from 2 to 8; or said acid or amino derivatives listed in claim 2.

4. A compound as claimed in claim 2 and corresponding to the formula:

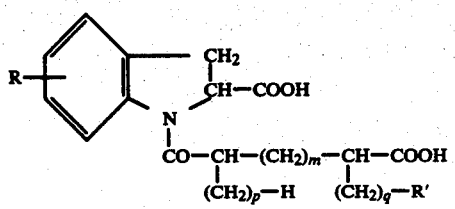

wherein R is hydrogen, alkyl or alkoxy with up to 4 carbon atoms, halogeno or trifluoromethyl; m is the integer 0 or 1; each of p and q is an integer from 0 to 2; and R' is hydrogen or R-phenyl; a mono- or bis-amide, the mono- or bis-lower (alkyl or ω-aminoalkyl) ester, a pharmaceutically acceptable alkali metal or ammonium salt of said acid, or an acid addition salt of said aminoalkyl ester.

5. A compound as claimed in claim 4, in which formula R is hydrogen, methyl, methoxy, fluoro, chloro or trifluoromethyl; each of m and p is the integer 1; q is the integer 1 or 2; and R' is hydrogen or phenyl, or a said acid or amino derivative listed in claim 4.

6. A compound as claimed in claim 4, wherein R is in the 5-indoline-position.

7. A compound as claimed in claim 4, in the form of its 2S-carboxy-indoline chiral epimer.

8. 1-(2,4-dimethyl-4-carboxybutanoyl)-indoline-2S-carboxylic acid; or a pharmaceutically acceptable alkali metal or ammonium salt thereof.

9. 1-[4-carboxy-4-(2-phenethyl)-butanoyl]-indoline-2S-carboxylic acid; or a pharmaceutically acceptable metal or ammonium salt thereof.

10. A compound as claimed in claim 7, and being the 1-(4-carboethoxy-2R,4R-dimethylbutanoyl)-indoline-2S-carboxylic acid; or a pharmaceutically acceptable alkali metal or ammonium salt thereof.

11. A compound as claimed in claim 7, and being the 1-(4-carboxy-2R,4R-dimethylbutanoyl)-indoline-2S-carboxylic acid; or a pharmaceutically acceptable alkali metal or ammonium salt thereof.

12. A compound as claimed in claim 7, and being the 1-(4-carboethoxy-2R-methylbutanoyl)-indoline-2S-carboxylic acid; or a pharmaceutically acceptable alkali metal or ammonium salt thereof.

13. A compound as claimed in claim 7, and being the 1-(4-carboxy-2R-methylbutanoyl)-indoline-2S-carboxylic acid; or a pharmaceutically acceptable alkali metal or ammonium salt thereof.

14. A compound as claimed in claim 7, and being the 1-(4-carboethoxy-2R-methyl-4R-phenethylbutanoyl)-indoline-2S-carboxylic acid; or a pharmaceutically acceptable alkali metal or ammonium salt thereof.

15. An antihypertensive and cardioactive pharmaceutical composition comprising a correspondingly effective amount of a compound as claimed in claim 1, together with a pharmaceutical excipient.

16. A method of treating hypertension or congestive heart failure in mammals, which consists in administering to said mammals in need thereof, an effective amount of a composition claimed in claim 15.

17. A compound as claimed in claim 4 wherein the chirality corresponds to the formula IIa:

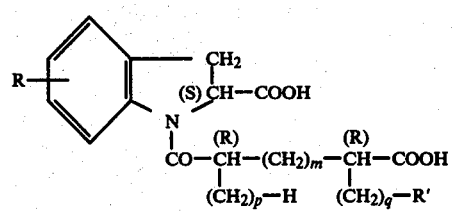

* * * * *